(12) United States Patent
Tai et al.

(10) Patent No.: US 8,877,489 B2
(45) Date of Patent: Nov. 4, 2014

(54) ULTRATHIN PARYLENE-C SEMIPERMEABLE MEMBRANES FOR BIOMEDICAL APPLICATIONS

(75) Inventors: Yu-Chong Tai, Pasadena, CA (US); Bo Lu, Pasadena, CA (US); Mark Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 34 days.

(21) Appl. No.: 13/355,426

(22) Filed: Jan. 20, 2012

(65) Prior Publication Data
US 2013/0143326 A1 Jun. 6, 2013

Related U.S. Application Data

(60) Provisional application No. 61/566,965, filed on Dec. 5, 2011.

(51) Int. Cl.
| | | |
|---|---|---|
| C12M 1/12 | (2006.01) | |
| C12M 1/00 | (2006.01) | |
| C12M 3/00 | (2006.01) | |
| A01N 1/00 | (2006.01) | |
| A01N 1/02 | (2006.01) | |

(52) U.S. Cl.
USPC .................. 435/297.1; 435/283.1; 435/284.1; 435/289.1; 435/297.2

(58) Field of Classification Search
USPC ........................................... 435/283.1–309.4
See application file for complete search history.

(56) References Cited

U.S. PATENT DOCUMENTS

| | | |
|---|---|---|
| 4,047,532 A | 9/1977 | Phillips et al. |
| 4,700,298 A | 10/1987 | Palcic et al. |
| 4,715,373 A | 12/1987 | Mazzocco et al. |
| 5,024,223 A | 6/1991 | Chow |
| 5,196,003 A | 3/1993 | Bilweis |

(Continued)

FOREIGN PATENT DOCUMENTS

| | | |
|---|---|---|
| JP | 11-009297 | 1/1999 |
| WO | WO 2005/082049 | 9/2005 |

(Continued)

OTHER PUBLICATIONS

Armstrong, J.K. et al., "The hydrodynamic radii of macromolecules and their effect on red blood cell aggregation," Biophys. J., 2004, vol. 87, pp. 4259-4270.

(Continued)

Primary Examiner — Nathan Bowers
Assistant Examiner — Lydia Edwards
(74) Attorney, Agent, or Firm — Knobbe Martens Olson & Bear, LLP

(57) ABSTRACT

Thin parylene C membranes having smooth front sides and ultrathin regions (e.g., 0.01 μm to 5 μm thick) interspersed with thicker regions are disclosed. The back sides of the membranes can be rough compared with the smooth front sides. The membranes can be used in vitro to grow monolayers of cells in a laboratory or in vivo as surgically implantable growth layers, such as to replace the Bruch's membrane in the eye. The thin regions of parylene are semipermeable to allow for proteins in serum to pass through, and the thick regions give mechanical support for handling by a surgeon. The smooth front side allows for monolayer cell growth, and the rough back side helps prevents cells from attaching there.

14 Claims, 9 Drawing Sheets

(56) References Cited

U.S. PATENT DOCUMENTS

| | | |
|---|---|---|
| 5,843,780 A | 12/1998 | Thomson |
| 6,117,675 A | 9/2000 | van der Kooy et al. |
| 6,156,042 A | 12/2000 | Aramant |
| 6,200,806 B1 | 3/2001 | Thomson |
| 6,231,879 B1 | 5/2001 | Li et al. |
| 6,254,628 B1 | 7/2001 | Wallace et al. |
| 6,264,941 B1 | 7/2001 | Baetge et al. |
| 6,299,895 B1 | 10/2001 | Hammang et al. |
| 6,303,136 B1 | 10/2001 | Li et al. |
| 6,322,804 B1 | 11/2001 | Dionne et al. |
| 6,337,198 B1 | 1/2002 | Levene et al. |
| 6,361,771 B1 | 3/2002 | Tao et al. |
| 6,436,427 B1 | 8/2002 | Hammang et al. |
| 6,582,903 B1 | 6/2003 | Rigler et al. |
| 6,627,422 B1 | 9/2003 | Li et al. |
| 6,642,048 B2 | 11/2003 | Xu et al. |
| 6,649,184 B2 | 11/2003 | Hammang et al. |
| 6,667,176 B1 | 12/2003 | Funk et al. |
| 6,669,719 B2 | 12/2003 | Wallace et al. |
| 6,712,837 B2 | 3/2004 | Akerfeldt et al. |
| 6,800,480 B1 | 10/2004 | Bodnar et al. |
| 6,833,269 B2 | 12/2004 | Carpenter |
| 6,852,527 B2 | 2/2005 | Chan et al. |
| 6,875,607 B1 | 4/2005 | Reubinoff et al. |
| 6,939,378 B2 | 9/2005 | Fishman et al. |
| 6,942,873 B2 | 9/2005 | Russell et al. |
| 7,005,252 B1 | 2/2006 | Thomson |
| 7,011,828 B2 | 3/2006 | Reubinoff et al. |
| 7,029,913 B2 | 4/2006 | Thomson |
| 7,107,124 B2 | 9/2006 | Green |
| 7,115,257 B1 | 10/2006 | Tao et al. |
| 7,135,172 B1 | 11/2006 | Loftus et al. |
| 7,141,369 B2 | 11/2006 | Cao |
| 7,147,648 B2 | 12/2006 | Lin |
| 7,217,569 B2 | 5/2007 | Thomson |
| 7,250,294 B2 | 7/2007 | Carpenter et al. |
| 7,297,539 B2 | 11/2007 | Mandalam et al. |
| 7,384,426 B2 | 6/2008 | Wallace et al. |
| 7,410,798 B2 | 8/2008 | Mandalam et al. |
| 7,413,734 B2 | 8/2008 | Mistry et al. |
| 7,413,902 B2 | 8/2008 | Bodnar et al. |
| 7,439,064 B2 | 10/2008 | Thomson et al. |
| 7,455,983 B2 | 11/2008 | Xu et al. |
| 7,504,257 B2 | 3/2009 | Reubinoff et al. |
| 7,541,186 B2 | 6/2009 | Reh et al. |
| 7,582,479 B2 | 9/2009 | Thomson |
| 7,601,525 B2 | 10/2009 | Batich et al. |
| 7,604,992 B2 | 10/2009 | Reubinoff |
| 7,695,967 B1 | 4/2010 | Russell et al. |
| 7,736,896 B2 | 6/2010 | Klimanskaya et al. |
| 7,749,726 B2 | 7/2010 | Chuck |
| 7,781,216 B2 | 8/2010 | Thomson |
| 7,794,704 B2 | 9/2010 | Klimanskaya et al. |
| 7,795,025 B2 | 9/2010 | Klimanskaya et al. |
| 7,820,195 B2 | 10/2010 | Kauper et al. |
| 7,824,671 B2 | 11/2010 | Binder et al. |
| 7,838,727 B2 | 11/2010 | Lanza et al. |
| 7,846,467 B2 | 12/2010 | Coroneo et al. |
| 7,855,068 B2 | 12/2010 | Cao |
| 7,875,296 B2 | 1/2011 | Binette et al. |
| 7,893,315 B2 | 2/2011 | Chung et al. |
| 7,910,369 B2 | 3/2011 | West et al. |
| 7,914,147 B2 | 3/2011 | Sharifzadeh et al. |
| 7,947,498 B2 | 5/2011 | Reubinoff et al. |
| 7,959,942 B2 | 6/2011 | Cottone et al. |
| 2002/0160509 A1 | 10/2002 | Reubinoff et al. |
| 2003/0054331 A1 | 3/2003 | Fraser et al. |
| 2003/0231791 A1 | 12/2003 | Torre-Bueno et al. |
| 2005/0031599 A1 | 2/2005 | Kooy et al. |
| 2005/0079616 A1 | 4/2005 | Reubinoff |
| 2005/0106554 A1 | 5/2005 | Palecek et al. |
| 2005/0164383 A1 | 7/2005 | Reubinoff et al. |
| 2005/0214345 A1 | 9/2005 | Leng et al. |
| 2005/0260747 A1 | 11/2005 | Reubinoff et al. |
| 2006/0002900 A1 | 1/2006 | Binder et al. |
| 2006/0078543 A1 | 4/2006 | Reubinoff et al. |
| 2006/0078545 A1 | 4/2006 | Carpenter |
| 2006/0104957 A1 | 5/2006 | Yiu et al. |
| 2006/0149194 A1 | 7/2006 | Conston et al. |
| 2006/0234376 A1 | 10/2006 | Mistry et al. |
| 2006/0235430 A1 | 10/2006 | Le et al. |
| 2006/0282128 A1 | 12/2006 | Tai et al. |
| 2007/0106208 A1 | 5/2007 | Uber et al. |
| 2007/0212777 A1 | 9/2007 | Reubinoff |
| 2008/0243224 A1 | 10/2008 | Wallace et al. |
| 2008/0299582 A1 | 12/2008 | Mandalam et al. |
| 2009/0004736 A1 | 1/2009 | Reubinoff |
| 2009/0074832 A1 | 3/2009 | Zussman et al. |
| 2009/0075373 A1 | 3/2009 | Reubinoff et al. |
| 2009/0104695 A1 | 4/2009 | Shushan et al. |
| 2009/0117639 A1 | 5/2009 | Carpenter |
| 2009/0123992 A1 | 5/2009 | Chin |
| 2009/0130756 A1 | 5/2009 | Klann et al. |
| 2009/0270982 A1 | 10/2009 | Torres et al. |
| 2009/0291495 A1 | 11/2009 | Carpenter et al. |
| 2009/0305405 A1 | 12/2009 | Carpenter et al. |
| 2009/0306772 A1 | 12/2009 | Tao et al. |
| 2010/0068141 A1 | 3/2010 | Kaushal et al. |
| 2010/0093091 A1 | 4/2010 | Reubinoff et al. |
| 2010/0137510 A1 | 6/2010 | Seliktar et al. |
| 2010/0144033 A1 | 6/2010 | Mandalam et al. |
| 2010/0173410 A1 | 7/2010 | Thomson et al. |
| 2010/0189338 A1 | 7/2010 | Lin et al. |
| 2010/0203633 A1 | 8/2010 | Mandalam et al. |
| 2010/0211079 A1 | 8/2010 | Aramant |
| 2010/0241060 A1 | 9/2010 | Roizman et al. |
| 2010/0272803 A1 | 10/2010 | Mistry et al. |
| 2010/0299765 A1 | 11/2010 | Klimanskaya et al. |
| 2010/0317101 A1 | 12/2010 | Mandalam et al. |
| 2011/0004304 A1 | 1/2011 | Tao et al. |
| 2011/0027787 A1 | 2/2011 | Chuck |
| 2011/0060232 A1 | 3/2011 | Lin et al. |
| 2011/0076320 A1 | 3/2011 | Coroneo |
| 2011/0091927 A1 | 4/2011 | Reubinoff et al. |
| 2011/0117062 A1 | 5/2011 | Klimanskaya et al. |
| 2011/0117063 A1 | 5/2011 | Klimanskaya et al. |
| 2011/0177594 A1 | 7/2011 | Shushan et al. |
| 2011/0189135 A1 | 8/2011 | Aharonowiz et al. |
| 2011/0236464 A1 | 9/2011 | Coffey et al. |
| 2011/0256623 A1 | 10/2011 | Thomson |
| 2013/0137958 A1 | 5/2013 | Tai et al. |
| 2013/0143326 A1 | 6/2013 | Tai et al. |
| 2013/0144399 A1 | 6/2013 | Tai et al. |

FOREIGN PATENT DOCUMENTS

| | | |
|---|---|---|
| WO | WO 2007/132332 | 11/2007 |
| WO | WO 2008/098187 | 8/2008 |
| WO | WO 2008/129554 | 10/2008 |
| WO | WO 2009/127809 | 10/2009 |
| WO | WO 2012/004592 | 1/2012 |
| WO | WO 2012/009377 A2 | 1/2012 |
| WO | WO 2012/149468 | 11/2012 |
| WO | WO 2012/149480 | 11/2012 |
| WO | WO 2012/149484 | 11/2012 |

OTHER PUBLICATIONS

Hsiao, A.Y. et al., "Microfluidic system for formation of PC-3 prostate cancer co-culture spheroids," Biomaterials, 2009, vol. 30, pp. 3020-3027.

Humayun, Mark et al., "Biocompatible substrate for facilitating interconnections between stem cells and target tissues and methods for implanting same," U.S. Appl. No. 61/481,037, filed Apr. 29, 2011, 149 pp.

Jackson, T.L. et al., "Human retinal molecular weight exclusion limit and estimate of species variation," IOVS, 2003, vol. 44, pp. 2141-2146.

Lee, C.J. et al., "Determination of human lens capsule permeability and its feasibility as a replacement for Bruch's membrane," Biomaterials, 2006, vol. 27, pp. 1670-1678.

Liu, M.C. et al., "A 3-D microfluidic combinatorial cell culture array," IEEE Proc. of MEMS 2009, Sorrento, Italy, pp. 427-430.

(56) References Cited

OTHER PUBLICATIONS

Lu, Bo et al., "A study of the autofluorescence of parylene materials for µTAS applications," Lab Chip, 2010, vol. 10, pp. 1826-1834.
Lu, J.T. et al., "Thin collagen film scaffolds for retinal epithelial cell culture," Biomaterials, 2007, vol. 28, pp. 1486-1494.
Roy, S. et al., "Silicon nanopore membrane technology for an implantable artificial kidney," Proc. of Transducers 2009, Denver, Colorado, USA, pp. 755-760.
Lu, Bo et al., "Ultrathin parylene-C semipermeable membranes for biomedical applications," IEEE International Micro Electro Mechanical Systems (MEMS '11), Cancun, Mexico, Jan. 23-27, 2011, pp. 505-508.
U.S. Appl. No. 13/181,279, filed Jan. 12, 2012, Humayun, et al.
"12mm Transwell with 0.4 um Pore Polyester Membrane Insert," [Online], Corning. Com, URL:http://catalog2.corning.com/Lifesciences/en-US/Shopping/PFProductDetails.aspx?productid=3460(Lifesciences)>>[retrieved on Jun. 12, 2009].
Algvere et al., "Transplantation of RPE in Age-Related Macular Degeneration: Observations in Disciform Lesions and dry RPE Atrophy, " Graefe's Arch Clin Exp Ophthalmol, vol. 235, Issue 3, 1997, pp. 149-158.
Binder S. et al., "Transplantation the RPE in AMD," Progress in Retinal and Eye Research, vol. 26, No. 5, Sep. 2007, pp. 516-554.
Chang et al., Cell and Protein Compatibility of Parylene-C Surfaces, Langmuir, vol. 23(23):11718-11725 (2007).
DeBoer et al., "Multiparameter Analysis of Primary Epithelial Cultures Grown on Cycloprore Membranes," Journal of Histochemistry and Cytochemistry, vol. 42, Issue 2, 1994, pp. 277-282.
Hannachi et al., "Cell Sheet Technology and Cell Patterning for Biofabrication," Biofabrication [Online], vol. 1, No. 2, p. 022002, Jun. 10, 2009, URL:http://iopscience.iop.org/1758-5090/1/2/022002/ [Retrieved on Jul. 17, 2012].
Huang, Yiming, et al. "Stem cell-based therapeutic applications in retinal degenerative diseases" Stem Cell Reviews and Reports, Humana Press Inc., NY. vol. 7, No. 2, Sep. 22, 2009, pp. 434-445.
International Search Report in PCT/US2011/043747 (WO 2012/009377), dated Jul. 24, 2012.
Kannan R. et al., "Stimulation of Apical and Basolateral VEGF-A and VEGF-C Secretion by Oxidative Stress in Polarized Retinal Pigment Epithelial Cells," Molecular Vision, vol. 12, 2006, pp. 1649-1659.
Lavik, E. B. et al., "Fabrication of Degradable Polymer Scaffolds to Direct the Integration and Differentiation of Retinal Progenitors," Biomaterials, vol. 26, Issue 16, Jun. 2005, pp. 3187-3196.
Lu, Bo et al. "Semipermeable parylene membrane as an artificial bruch's membrane" 2011 16th International Solid-State Sensors, Actuators and Microssytems Conference (Transducers 2011): Beijing, China Jun. 5-9 2011. pp. 950-953.
Lu, JT et al., Thin collagen film scaffolds for reitnal epithelial cell culture, Biomaterials, vol. 28:1486-1494 (2007).
Morris et al., Cryopreservation of murine embryos, human spermatazoa and embryonic stem cells using a liquid nitrogen-free controlled rate freezer, Reproductive Biomedicine Online, vol. 13(3):421-426 (2006).
Pereira-Rodrigues et al., Modulation of hepatocarcinoma cell morphology and activity by parylene-C coating on PDMS, PLoS One, vol. 5(3):e9667 (2010).
Neeley, W. et al., "A Microfabricated Scaffold for Retinal Progenitor Cell Grafting," Biomaterials, vol. 29, Issue 4, Feb. 2008, pp. 418-426.
Redenti, S et al., "Engineering Retinal Progenitor Cell and Scrollable poly(glycerol-sebacate) composites for Expansion and Subretinal Transplantation," Biomaterials, vol. 30, Issue 20, Apr. 9, 2009, pp. 3405-3414.
Redenti, S et al., "Retinal Tissue Engineering using Mouse Retinal Progenitor Cells and a Novel Biodegradable, Thin-Film Poly(e-caprolactone) Nanowire Scaffold," J Ocul Biol Dis Infor., vol. 1, Issue 1, May 22, 2008, pp. 19-29.
Sodha, S. "A Microfabricated 3-D stem Cell Delivery Scaffold for Retinal Regenerative Therapy," Thesis, Master of Engineering in Biomedical Engineering, Massachusetts Institute of Technology, Jun. 2009.
Sodha, S. et al., "Microfabrication of a Three-Dimensional Polycaprolactone Thin-Film Scaffold for Retinal Progenitor Cell Encapsulation," J Biomater Sci Polym Ed., vol. 22, Issue 4-6, Jun. 21, 2011, pp. 443-456.
Stanzel B. V. et al., "Culture of Human RPE from Aged Donors on a Potential Bruch's Membrane Prosthesis" Invest Ophthalmol Vis Sci, [Online] vol. 47, 2006, URL:http://abstracts.iovs.org/cgi/content/abstract/47/5/1407?maxtoshow=&HITS=10&hits=10&RESULTFORMAT=1&author1=stanzel&andorexacttitle=and&andorexacttitleabs=and&andorexactfulltext=and&searchid=l&FIRSTINDEX=O&sortspec=relevance&resourcetype=HWCIT,HWELTR> [retrieved on Jun. 12, 2009].
Stanzel et al., "Towards Prosthetic Replacement of Bruch's Membrane: Comparison of Polyester and Electrospun Nanofiber Membranes" Invest Ophthalmol Vis Sci, [Online] vol. 48, 2007, URL:http://abstracts.iovs.org/cgi/content/abstract/48/5/5085?maxtoshow=&HITS=10&hits=10&RESULTFORMAT=1&author1=stanzel&andorexacttitle=and&andorexacttitleabs=and&andorexactfulltext=and& searchid=l&FIRSTINDEX=O&sortspec=relevance&resourcetype=HWCIT,HWELT R> [retrieved on Jun. 12, 2009].
Tezcaner, A et al., "In Vitro Characterization of Micropatterned PLGA-PHBV8 Blend Films as Temporary Scaffolds for Photoreceptor Cells," J Biomed Mater Res vol. 86A, Issue 1, Oct. 23, 2007, pp. 170-181.
Wang, Renxin, et al. "Fabrication and characterization of a parylene-based three-dimensional microelectrode array for use in retinal prosthesis" Journal of Microelectromechanical Systems, IEEE Service Center, US, vol. 19, No. 2, Apr. 1, 2010 pp. 367-374.
IPRP and Written Opinion of the International Search Authority in PCT/US2011/043747 (WO 2012/009377), dated Jan. 15, 2013.

TOP VIEW WITH CELLS

TOP VIEW

BOTTOM VIEW

TOP VIEW

BOTTOM VIEW

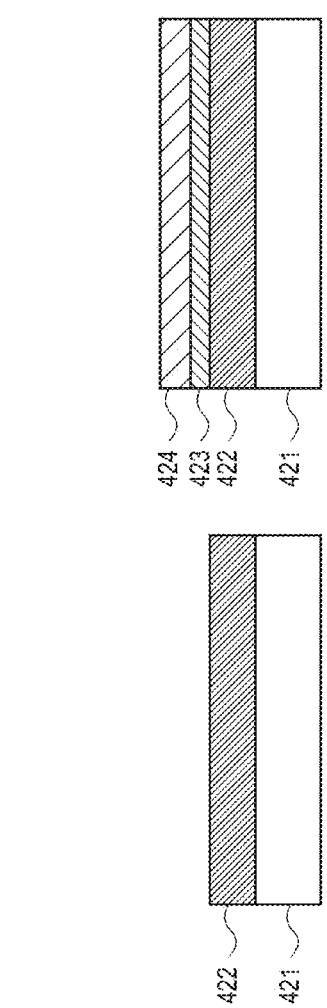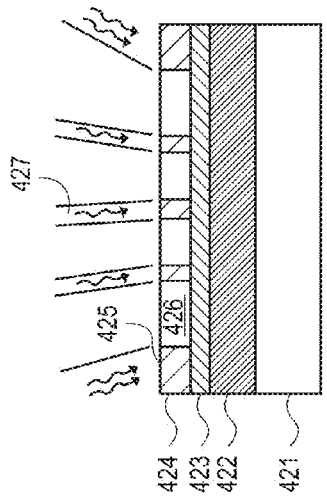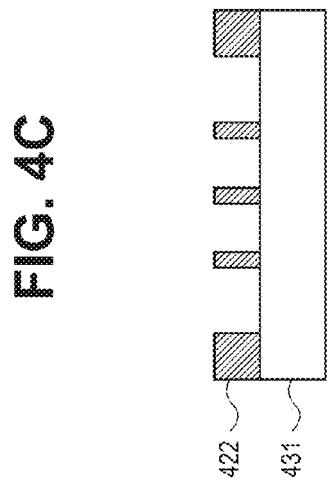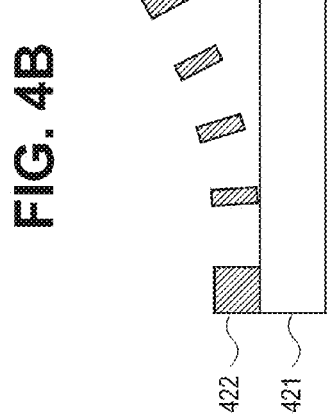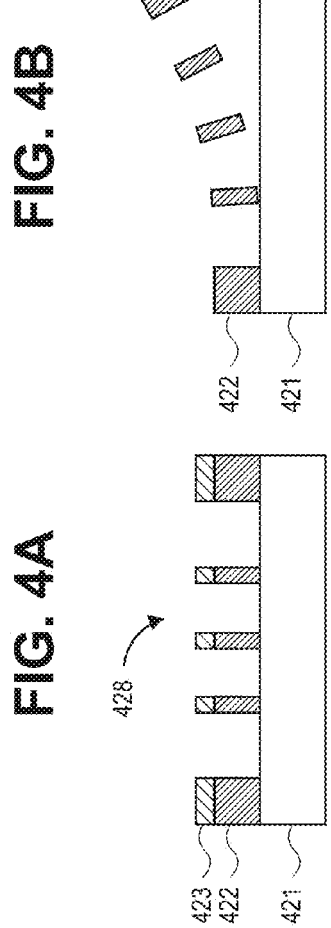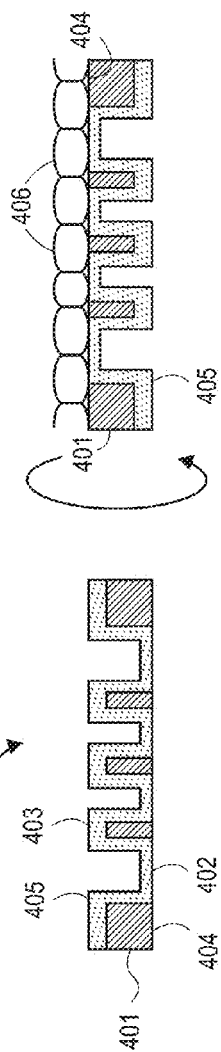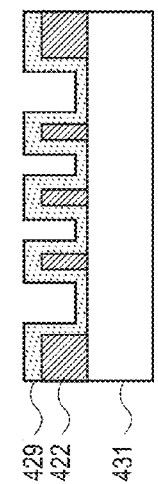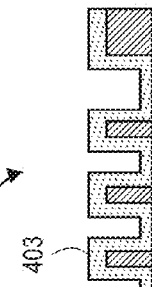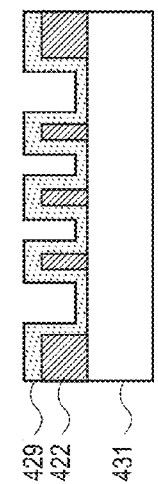

ULTRATHIN PARYLENE-C SEMIPERMEABLE MEMBRANES FOR BIOMEDICAL APPLICATIONS

CROSS-REFERENCES TO RELATED APPLICATIONS

This application claims the benefit of U.S. Provisional Patent Application No. 61/566,965, filed Dec. 5, 2011, which is hereby incorporated by reference in its entirety for all purposes.

International Application No. PCT/US2011/043747, filed Jul. 12, 2011, and U.S. Provisional Application No. 61/481,037, filed Apr. 29, 2011, are hereby incorporated by reference in their entireties for all purposes.

STATEMENT AS TO RIGHTS TO INVENTIONS MADE UNDER FEDERALLY SPONSORED RESEARCH OR DEVELOPMENT

NOT APPLICABLE

BACKGROUND

1. Field of the Art

Embodiments of the present invention generally relate to biomedical membranes and, in particular, to ultrathin (e.g., between 0.01 μm to 5 μm thick) parylene C membranes that have exhibited permeability that is ideal for monolayer biological cell growth.

2. Description of the Related Art

Biological cells are often grown on membranes. For optimal growth of on on-membrane cell culture, the membranes must be permeable to nutrients (and waste from cells), such as proteins in serum. Membranes with pores that are large enough to allow proteins to flow through are used extensively in laboratories and are finding new applications as analysis equipment becomes smaller and more efficient.

Porous membranes are widely used in Micro Total Analysis System (gTAS) and Lab-on-a-Chip (LOC) applications, allowing chemical or biological reagents transportations and filtration. Among different types of membranes, commercially available track-etched porous membranes are one of the most popular choices, with various sizes of holes in submicron and micron (μm) ranges. Track etching involves heavy-ion bombardment of thin films and then chemical etching to reveal the tracks into holes.

Parylene, a generic name for members of a series of polypxylylene) polymers, is generally biocompatible. Of the common types of parylene, parylene C is perhaps the most widely used in industry. Parylene C is sometimes referred to with a dash, i.e., "parylene-C," and sometimes is abbreviated as "PA-C." Its demonstrated bio-compatibility as a United States Pharmacopeial Convention (USP) Class VI biocompatible polymer makes it suitable for medical devices. However, it is not porous or considered permeable. In fact, it is used extensively in industry as a conformal coating for electronics and medical devices because it is water tight and essentially pinhole-free when chemical vapor deposited in extremely thin layers.

BRIEF SUMMARY

Generally, devices, systems, and methods for manufacturing a semipermeable parylene C membrane are disclosed. Parylene C—which has been found to be permeable to proteins in serum at ultrathin thicknesses (e.g., 0.01 μm to 5 μm thick)—is manufactured into a membrane having a smooth front side and tiny hills and valleys on the back side, such that it has a variable thickness. The hills and valleys, which can be stepwise-edged like a city skyline or histogram, can be manufactured using lithographic techniques.

One way of manufacturing such a membrane is to etch a relatively thick parylene film with tiny, through-hole perforations, lay it on a smooth substrate, and deposit an ultrathin layer of parylene over the perforated thick layer. The resulting parylene membrane is then peeled off of the substrate. The side of the membrane that was against the substrate is smooth, as the ultrathin layer of parylene covers the openings of the perforations. The opposite side of the membrane remains rough with hills and valleys because the ultrathin layer of deposited parylene was not enough material to fill in the etched perforations.

Embodiments of the present invention relate to a synthetic semipermeable membrane apparatus. The apparatus includes a membrane having a smooth front side, a back side, and spatially interspersed thin and thick regions between the smooth front side and the back side, the thin regions being a predetermined thickness of parylene, the predetermined thickness selected from a thickness between 0.01 μm to 5 μm, such as 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm. The thick regions comprise parylene or another material and are at least 2 times thicker than the predetermined thickness of the thin regions, and the interspersion of the thin and thick regions occur in a random or patterned array with an average feature size of about 1 μm to 10 μm, such as 1, 2, 3, 4, 5, 6, 7, 8, 9, or 10 μm.

Some embodiments relate to a synthetic semipermeable membrane apparatus, including a supporting film having a plurality of through perforations extending from a first side to an opposing, second side of the supporting film, and a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm) thin parylene layer covering an opening of each perforation of the supporting film.

Some embodiments relate to a process for fabricating a synthetic semipermeable membrane. The process includes providing a supporting film having through perforations extending from a first side to an opposing, second side of the supporting film, laying the first side of the supporting film against a smooth substrate surface, depositing a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm) thin parylene layer over the supporting film sufficient to cover a bottom of each perforation of the supporting film to form a membrane with a smooth first side, and removing the membrane from the smooth substrate surface.

Some embodiments relate to a method of using a synthetic semipermeable membrane, the method including providing a membrane that has a supporting film having a plurality of through perforations extending from a first side to an opposing, second side of the supporting film and a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8 and 5.0 μm) thin parylene layer covering an opening of each perforation of the supporting film wherein the covered openings of the perforations are even with a surface of the first side of the supporting film, thereby forming a substantially smooth surface on the first side. The method further includes diffusing molecules through the membrane.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 4A illustrates depositing an initial thick parylene layer in a manufacturing process for a semipermeable membrane in accordance with an embodiment.

FIG. 4B illustrates a metal and photoresist application step in the manufacturing process of FIG. 4A.

FIG. 4C illustrates a photolithographic exposure step in the manufacturing process of FIG. 4A.

FIG. 4D illustrates an etching step in the manufacturing process of FIG. 4A.

FIG. 4E illustrates a peeling of the thick layer step in the manufacturing process of FIG. 4A.

FIG. 4F illustrates an attachment of the thick layer to another substrate in the manufacturing process of FIG. 4A.

FIG. 4G illustrates deposition of an ultrathin layer of parylene in the manufacturing process of FIG. 4A.

FIG. 4H illustrates the completed membrane removed from the second substrate in the manufacturing process of FIG. 4A.

FIG. 4I illustrates the membrane being used to grow a monolayer of cells after the manufacturing process of FIG. 4A.

DETAILED DESCRIPTION

Figure 1A:
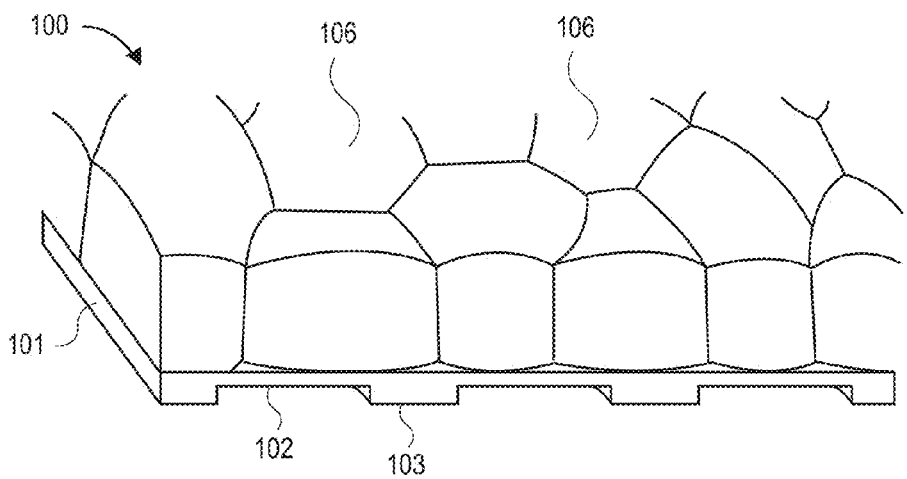
FIG. 1A is an oblique, cut-away top view of a semipermeable membrane growing a monolayer of cells in accordance with an embodiment.

Generally, devices, systems, and methods for manufacturing a semipermeable parylene C membrane are disclosed. A membrane with ultrathin (e.g., 0.01 µm to 5 µm thick) parylene regions is arranged to have a smooth side and a spatially variable thickness. The smooth side can be used to grow a monolayer of cells, while the bumps or undulations on the second side prevent cell growth on the second side. The ultrathin portions of the parylene are permeable to protein-sized molecules but impermeable to cells, which are on the order of 4 µm (for tiny photoreceptor rod and cone cells of the retina) to greater than 20 µm. The thicker portions of the membrane, which are interspersed with the thin portions, make the membrane stronger, less prone to folding or undulating, and generally easier to handle for surgeons.

Prior art porous membranes have been found to have disadvantages. First, the fabrication of small holes (i.e., <0.1 µm) is difficult to perform reliably. Therefore, in some applications where the cut-off selective size of the particles has to be smaller than 0.1 µm, porous membranes usually are not capable for biological applications. Second, when used in on-membrane cell culture applications, the porous topology may disturb the adherence and morphology of biological cells. The nooks and crannies of the pores present a non-smooth, variable surface, which is suboptimal for the growth of even cell monolayers. This can make the in vitro cultured cells very different from cells growing in their in vivo natural environment.

Materials that are naturally semipermeable are known, such as collagen and polydimethylsiloxane (PDMS). However, the surfaces of these semipermeable materials are often sponge-like. They are often not biocompatible, so they are not proper for implantation applications. Furthermore, they are difficult to reliably pattern into desired shapes and designs.

Parylene (including all the parylene derivatives such as parylene N, C, D, HT, AM, A, etc.) has been shown to be a superior biocompatible material, but it is usually used as a protective coating to prevent harmful large molecules from going through it. The inventors have not only determined how to use parylene as a permeable material, but they have also performed an in-depth study of the permeability of ultrathin parylene C to optimize the "thickness design" of parylene semi-permeable membranes. It has been found that parylene is permeable below some thicknesses, and the thinner the parylene, the more permeable it is. Furthermore, it is proposed that parylenes with thicknesses from 0.01 µm to 5 µm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 µm) can readily be used as semipermeable membranes in medical applications when coupled with thicker frames and supporting films.

Technical advantages of some of the embodiments are many. The smooth surface of the front side of a membrane is advantageous for cell growth than rough or spongy surfaces. The thin parylene areas allow nutrients and cell waste to pass through the membrane, while the thick areas give mechanical support and rigidity so that the membrane is less prone to tearing, folding, undulating, etc. during implantation. The thickness of the ultrathin parylene can be scaled for growing any cell type in a monolayer for implantation in the body. For example, retinal pigment epithelium (RPE) can be grown in a monolayer on the membrane. Cartilage trabeculae, heart muscle, and other cells can be grown in a monolayer as well. Besides facilitating in vitro perfusion cell culture, semipermeable parylene-C membrane also has use in the in vivo replacement of a Bruch's membrane in the eye for age-related macular degeneration. Bruch's membrane allows the passage of molecules with MW below 75 kDa.

An embodiment may be able to replace impaired human semipermeable tissue membranes anywhere in the human body, not just the Bruch's membrane. For example, the human lens capsule and collagen film can use parylene C membranes thinner than 0.30 µm.

As a proof of design, ultrathin parylene C membranes with thicknesses ranging from 0.15 µm to 0.80 µm have been experimentally verified. At least four different thicknesses (i.e., 0.15 µm, 0.30 µm, 0.50 µm, and 0.80 µm) of parylene C membranes manufactured on perforated support films were subject to diffusion studies using fluorescein isothiocyanate (FITC)-dextran molecules of different molecular weights (MWs) at body temperature (37° C.; 98.6° F.). A diffusion coefficients for each of five molecules (i.e. 10 kDa, 40 kDa, 70 kDa, 125 kDa, and 250 kDa) was obtained by fitting concentration-time curves into the equation:

$$C_2 = \frac{C_0 V_1}{V\left(1 - \exp\left(-\frac{Dt}{\tau h}\right)\right)} \quad \text{Eqn. 1}$$

where $$\tau = \frac{\left(V_1 + \frac{A_{\mathit{eff}} h}{2}\right)\left(V_2 + \frac{A_{\mathit{eff}} h}{2}\right)}{A_{\mathit{eff}} V} \quad \text{Eqn. 2}$$

where $C_0$ is the initial concentration on a first side of the membrane, $C_2$ is the concentration on the second side of the membrane (where $C_2$ at the start of each experiment is 0), $V_1$ and $V_2$ are the volumes of liquid on the respective sides of the membrane and $V=V_1+V_2$ (i.e., the total volume), h is the thickness of the ultrathin regions of the membrane (i.e., 0.15 µm, 0.30 µm, 0.50 µm, and 0.80 µm), and $A_{\mathit{eff}}$ is the effective area of the ultrathin portion of the membrane.

Because the membrane's thick regions were 20-µm diameter holes with a center-to-center spacing of 30 µm, $A_{\mathit{eff}}$ for all the tested membranes is:

$$A_{\mathit{eff}} = \frac{\pi (0.10 \ \mu m)^2}{0.30 \ \mu m \times 0.30 \ \mu m} \quad \text{Eqn. 3}$$

After obtaining the diffusion coefficients, the theoretical MW exclusion limit was then calculated for each thickness of film by extrapolating the linear relationship between the diffusion coefficients an the natural log of MW (i.e., ln(MW)) to a diffusion coefficient of zero. The results of this calculation are tabled in Table 1. Also tabled are respective exclusion radiuses (and diameters), calculated from the MWs of the FITC-dextran molecules.

TABLE 1

| Thickness (µm) | Exclusion MW (kDa) | Exclusion radius (µm) | Exclusion diameter (µm) |
|---|---|---|---|
| 0.15 | 1,302 | 0.02560 | 0.05120 |
| 0.30 | 1,008 | 0.02262 | 0.04524 |
| 0.50 | 291 | 0.01239 | 0.02478 |
| 0.80 | 71 | 0.0625 | 0.01250 |

Determining exclusion diameters of certain thicknesses of parylene is only part of the solution. While an ultrathin material may work in a laboratory, it may not be suitable in real-world situations.

Working with extremely thin parylene is difficult. To facilitate and strengthen the mechanical bending, stretching, and handling of ultrathin parylene, a thick supporting substrate design is disclosed. The supporting substrate is preferably thicker (e.g., 1-30 µm) than the ultrathin layers, such as two times as thick as the ultrathin layer. It can have various geometries, such as a mesh, net, pore, etc. geometry.

Further, a new substrate having an ultrathin parylene membrane with its back filled with some extremely permeable materials, such as silicone or hydrogels, is proposed for certain applications.

U.S. Patent Application Publication No. 2011/0236461 A1 to Coffey et al., published Sep. 29, 2011 (hereinafter "Coffey"), describes a polymer membrane for supporting the growth of retinal pigmented epithelial (RPE) cells in the human eye. Coffey discloses membrane pores between 0.2 µm and 0.5 µm in diameter (Coffey paragraph [0009]). The pore diameters in Coffey are substantially larger than exclusion diameters present in parylene C at the 0.01- to 5-µm thicknesses presented in this application (e.g., 0.0512 µm diameter; see Table 1). Furthermore, Coffey teaches that its membrane is preferably made from a hydrophilic polymer, such as polyester (see, e.g., Coffey paragraphs [0024] and [0043]), where parylene is characteristically hydrophobic.

The figures will be used to further describe aspects of the application.

Figure 1B:
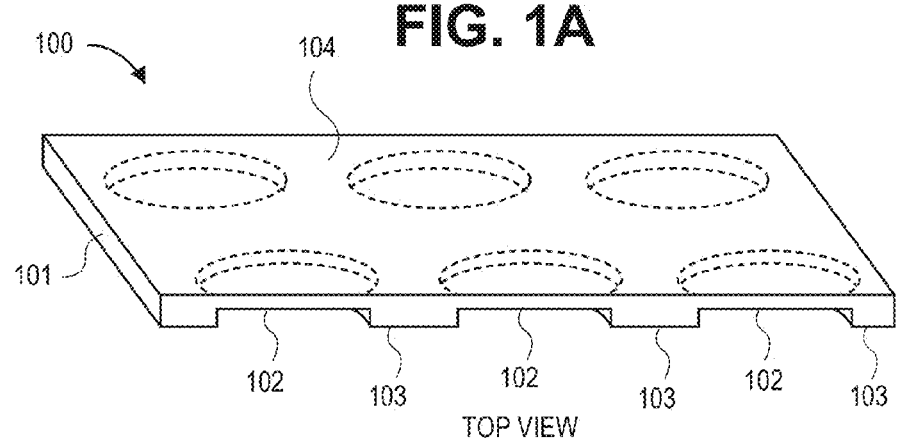
FIG. 1B is an oblique, cut-away top view of the semipermeable membrane of FIG. 1A without the cells.
Figure 1C:
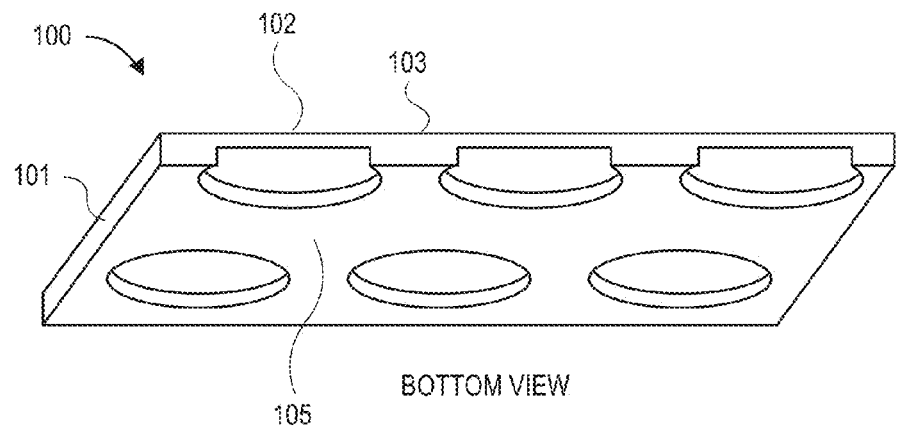
FIG. 1C is an oblique, cut-away bottom view of the semipermeable membrane of FIG. 1B.

FIGS. 1A-1C are oblique, cut-away views of a semipermeable membrane in accordance with an embodiment. FIG. 1A shows cells 106 growing on top of the membrane, while FIG. 1B omits the cells. FIG. 1C shows a bottom view of the membrane.

Biocompatible membrane system 100 includes membrane 101 having a front, top side 104 and a back, bottom side 105. Orientation terms of "front," "top," "back," "bottom," etc. are for the convenience of the reader and are not limiting as to absolute orientation. Front side 104 is smooth, having no salient protrusions or recesses that inhibit the natural formation of cells growing as a monolayer. Back side 105 is relatively rough, inhibiting or reducing the growth of cells.

Membrane 101 includes thin regions 102 interspersed with thick regions 103. In this embodiment, thick regions 103 are substantially contiguous with one another, and thin regions 102 comprise cylindrical recesses in the membrane. Thin regions 102 are interspersed in a regular, grid-like patterned array on membrane 101. In some embodiments, a random array, as opposed to one with a recognizable pattern, can be interspersed on the membrane. Embodiments having a combination of patterned and random arrays are also contemplated.

On front side 104, thin regions 102 flow cleanly with thick regions 103 to form a smooth surface as shown in FIG. 1B. On back side 105, thin regions 102 abruptly change to the plateaus of thick regions 103, forming a rough surface.

The thin regions are of a predetermined thickness, predetermined based on a permeability desired. For example, to allow proteins having a molecular weight of 70 kDa or smaller to flow through while inhibiting molecules having a molecular weight of over 100 kDa, the thickness of the thin regions can be engineered to be 0.80 µm thick (see Table 1).

The thick regions can be 2, 3, 4, 5, or 10 (and gradations in between) or more times thicker than the thin sections. Their increased thickness allows the entire membrane to be more easily handled. In the exemplary embodiment, thick regions 103 are 3 times the thickness of thin regions 102. In certain applications, thicknesses of more than 6 µm may be unwieldy. In some other cases, thick region thicknesses between 1 µm and 30 µm (such as 2, 3, 4, 5, 6, 7, 8, 9, 10, 11, 12, 13, 14, 15, 16, 17, 18, 19, 20, 21, 22, 23, 24, 25, 26, 27, 28, and 29 µm) thick can be used.

In other embodiments, the thin regions can be substantially contiguous with one another, with the thick regions comprising protrusions from the back side of the membrane. That is, instead of a bunch of holes as shown in FIG. 1C, there can be a bunch of mounds or other protrusions from an otherwise thin membrane.

"Substantially contiguous" regions include those that are flat with respect to each other without barriers or whose barriers are less than 10, 15, 20, or 25% of the respective regions' widths or as otherwise known in the art.

Figure 2A:
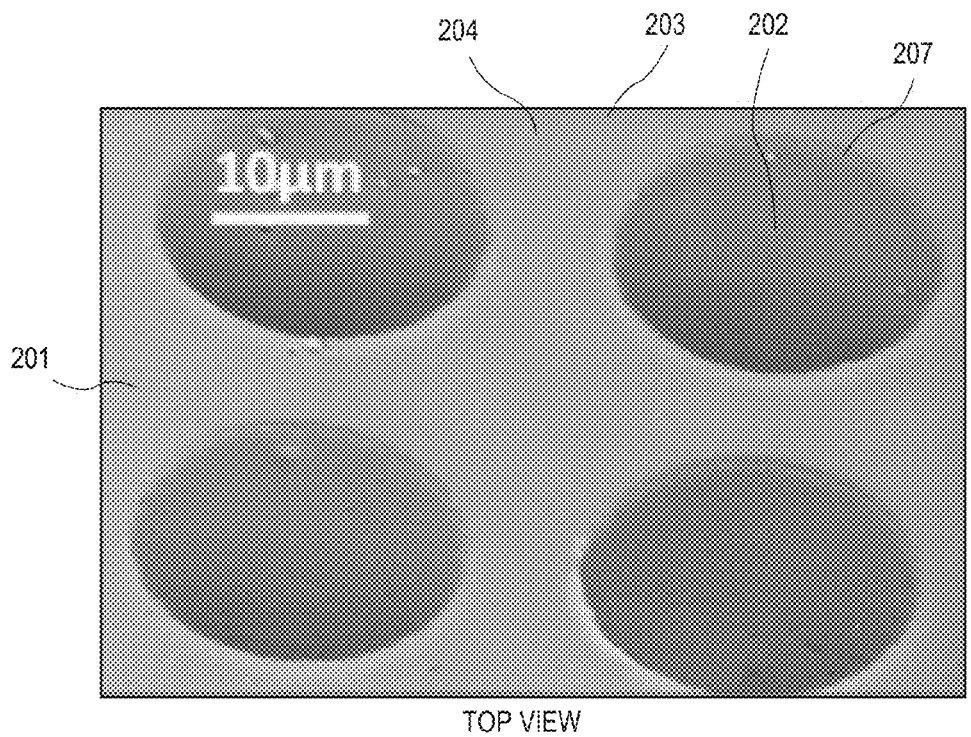
FIG. 2A is a scanning electron microscope (SEM) image of a top side of a semipermeable membrane manufactured in accordance with an embodiment.
Figure 2B:
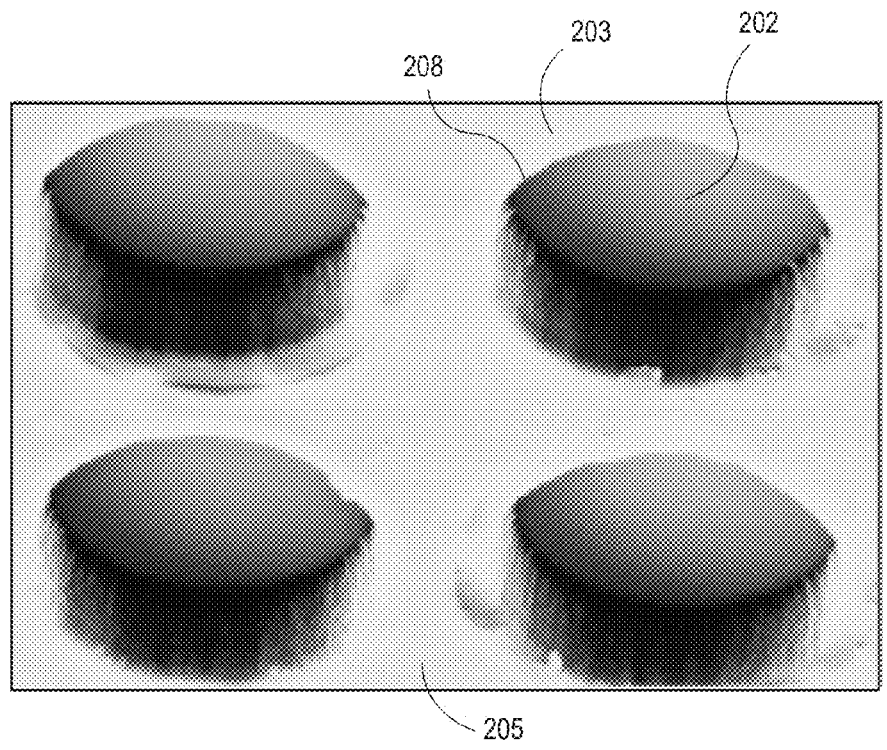
FIG. 2B is a scanning electron microscope (SEM) image of a bottom side of the semipermeable membrane of FIG. 2A.

FIGS. 2A-2B are scanning electron microscope (SEM) images of top and bottom sides of a semipermeable membrane manufactured in accordance with an embodiment.

In FIG. 2A, thin regions 202 of membrane 201 are almost transparent as seen from top side 204. They exhibit a drumhead like appearance, stretching over openings 207 in thick regions 203. Thicknesses of between 0.1 µm to 10 µm are considered to be a good range for many biological cells, allowing diffusion of proteins in serum to flow through the membrane. Thicknesses between 0.15 µm to 0.8 µm have been studied in depth. Thick regions of 3 µm to 4 µm thick allow a surgeon to manipulate the membrane with less chance of tearing, fold back, or undulation.

In FIG. 2B, recess 208 appears as a hole in thick region 203, bottoming out with thin region 202. The walls of recess 208 have been coated with an ultrathin layer of parylene to approximately the same thickness as the thin regions 202 as a result of a chemical vapor deposition (CVD) process described below.

Figure 3:
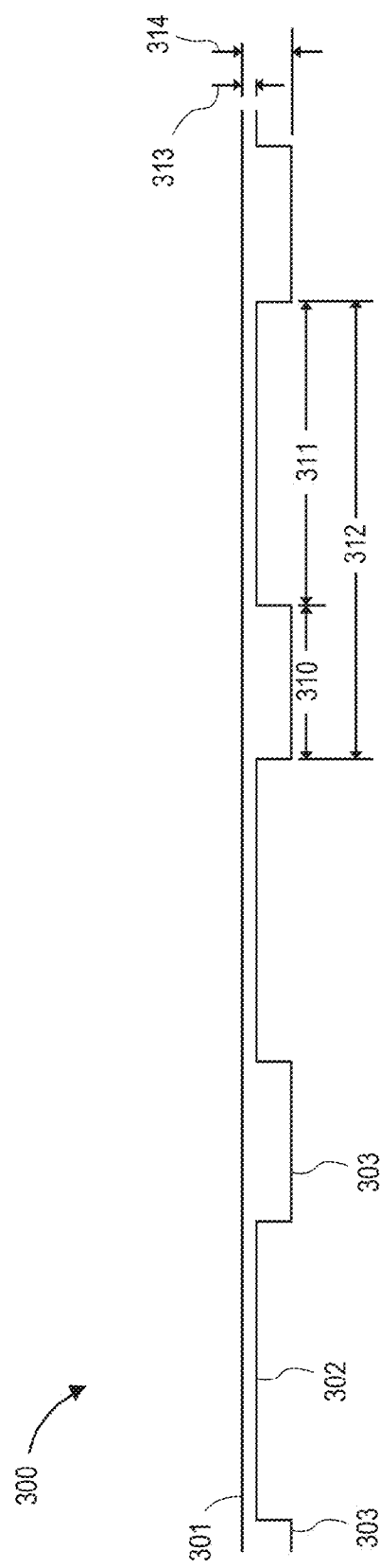
FIG. 3 is a side, elevation view of a semipermeable membrane in accordance with an embodiment.

FIG. 3 is a side, elevation view of a semipermeable membrane in accordance with an embodiment. Substrate 300 includes membrane 301 with thick regions 303 interspersed with repeating thin regions 302. Average feature size 310 of the plateaus between the repeating thin regions is about 10 µm (e.g., 7, 8, 9, 10, 11, or 12 µm). The thin regions are about 20 µm (17, 18, 19, 20, 21, or 22 µm) in diameter. The average, edge-to-edge (or center-to-center) pitch 312 is 30 µm (e.g., 26, 27, 28, 29, 30, 31, 32 µm). Thin region thickness 313 is 1 µm, while thick region thickness 314 is 3-4 µm. This spacing has been found to inhibit or reduce growth of cells that are about 20 µm in length.

FIGS. 4A-4H illustrate a manufacturing process for a semipermeable membrane in accordance with an embodiment.

As shown in FIG. 4A, an 8-µm thick supporting film 422 of parylene C is deposited on a cleaned, HMDS- (hexamethyldisilazane- or hexamethyldisiloxane-) treated silicon substrate 421. As shown in FIG. 4B, aluminum 423 is deposited on the parylene C supporting film 422 as an etching mask, followed by photoresist layer 424. As shown in FIG. 4C, photoresist layer 424 is illuminated in a random or patterned array using light 427. The photoresist becomes insoluble in regions 425 and soluble in regions 426. Soluble photoresist 426 is then washed away. As shown in FIG. 4D, wet-etching and reactive-ion etching (RIE) is used to etch 20 µm-diameter holes through supporting film 422 down to silicon substrate 421, to create array 428.

As shown in FIG. 4E, the now-perforated parylene layer 422 is removed from silicon substrate 421. As shown in FIG. 4F, perforated parylene layer 422 is attached to a different HDMS-treated silicon substrate 431. As shown in FIG. 4G, ultrathin parylene C film 429 (e.g., 0.15 µm to 0.80 µm thick) is then deposited on supporting film 422. The chemical vapor deposition (CVD) process results in a thin layer of parylene coating the walls as well as the bottom of the recesses. As shown in FIG. 4H, the completed membrane is peeled off, reversed and treated with $O_2$ plasma. The entire membrane, including both its thick and thin sections, is parylene, such as parylene C.

Manufactured membrane 401 has front side 404 (on the bottom in the figure) and back side 405 (on the top in the figure). Thin sections 402 are interlaced with thick sections 403 in pattern 428.

FIG. 4I illustrates membrane 401 being used to grow a monolayer of cells. The membrane has been rotated so that front side 404 faces up and back side 405 faces down. Cells 406 grow on smooth, front side 404 of membrane 401. Cells can be grown on the membrane in any orientation.

Figure 5:
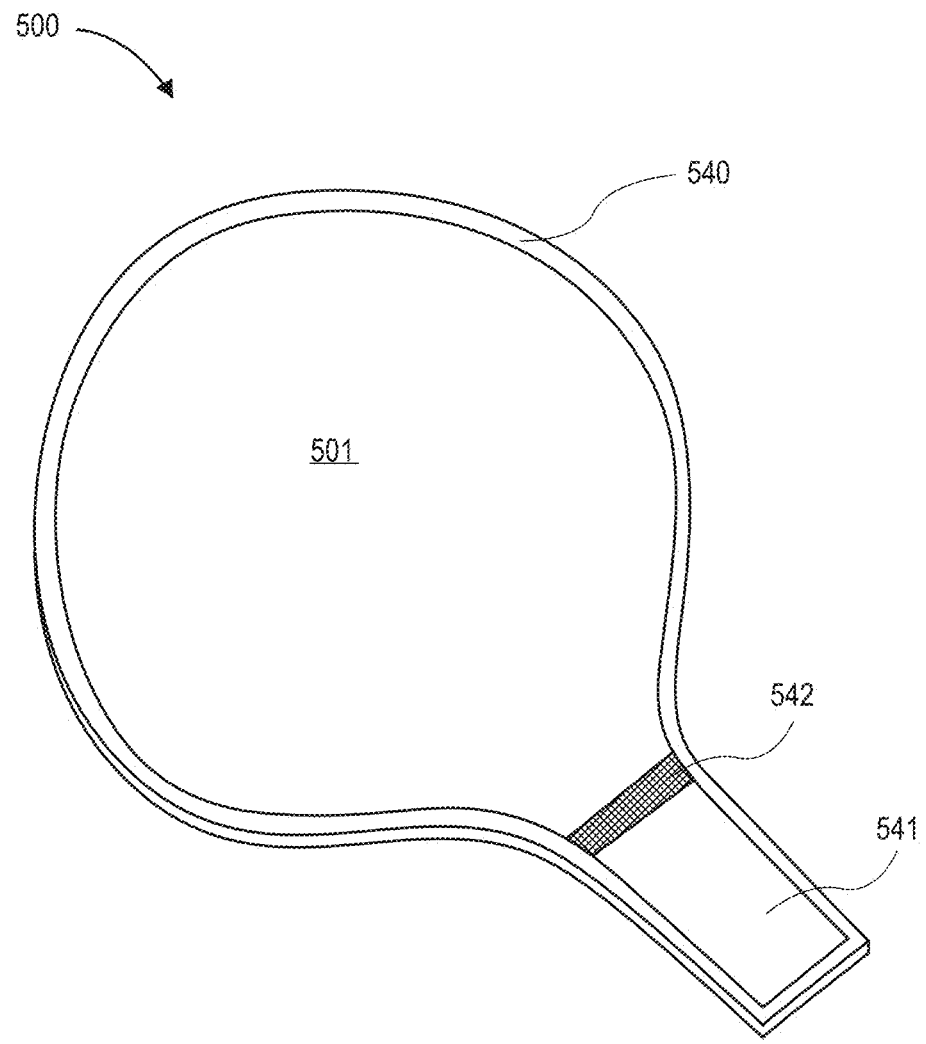
FIG. 5 illustrates an implantable membrane in accordance with an embodiment.

FIG. 5 illustrates an implantable membrane in accordance with an embodiment. Implantable membrane system 500 includes membrane 501 having tiny interlaced regions of ultrathin and thick biocompatible parylene. Frame 540 surrounds membrane 501 with a thick, relatively sharp edge that prevents or retards cells from migrating from a front, smooth side of the membrane to the back. Not only does frame 540 prevent or retard cells from migrating, but the relatively pointy and sharp edges of the rough side of the membrane prevents cells from gaining a foothold on the back side of the membrane. In this way, a surgeon can maximize the healthy monolayer growth of cells on one side of the membrane while minimizing undesirable cells on the back of the monolayer. This can be important in some applications, such as replacing the RPE behind the retina in the eye.

Tab 541 allows a surgeon's forceps or tool to hold the membrane, with cut-off section 542, or as otherwise described in U.S. Patent Application No. 61/481,037, filed Apr. 29, 2011.

Figure 6:
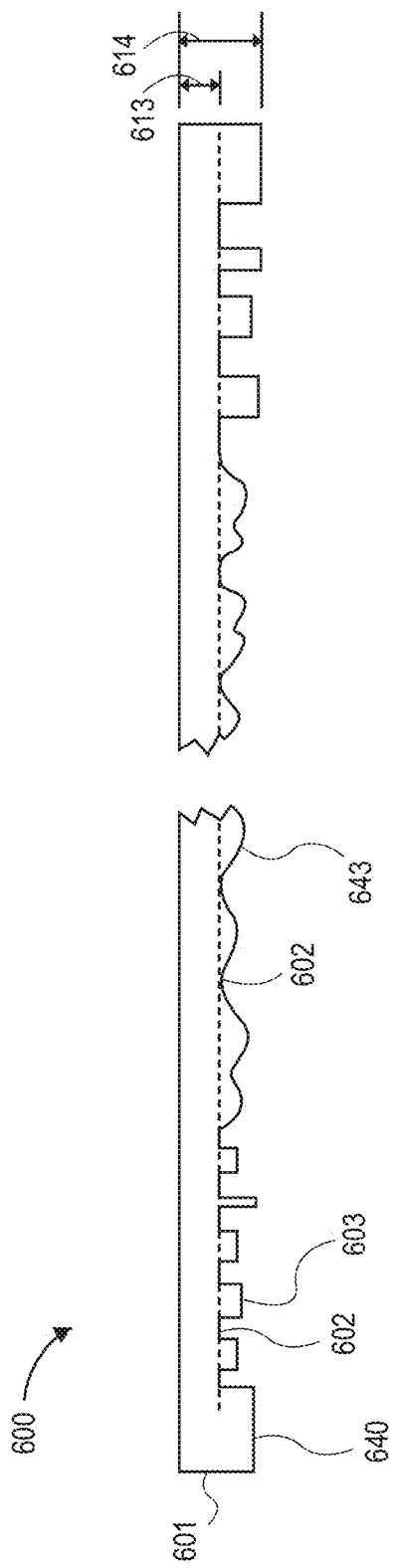
FIG. 6 is a side, elevation view of a semipermeable membrane with sharp and soft features in accordance with an embodiment.

FIG. 6 is a side, elevation view of a semipermeable membrane with sharp and soft features in accordance with an embodiment. Membrane system 600 includes membrane 601 with thin regions 602 of predetermined thickness 613.

Near circumference ring 640, membrane 601 includes thick regions 603 that have rectangular cross sections. Farther away from circumference ring 640, near the center of membrane 601, are thick regions 643 having rounded cross sections. Thick regions 603 have relatively sharp features with respect to thick regions 643, and thick regions 643 have relatively smooth features in comparison with thick regions 603.

Having relatively sharp regions near the circumference can retard or prevent cells that do happen to migrating around the edges of the membrane from growing on the membrane. Near the center, where there is less of a chance of cells migrating, the hills and valleys of the thick and thin regions can be smooth so that the membrane is better accepted during implantation and more compatible with the body.

Figure 7:
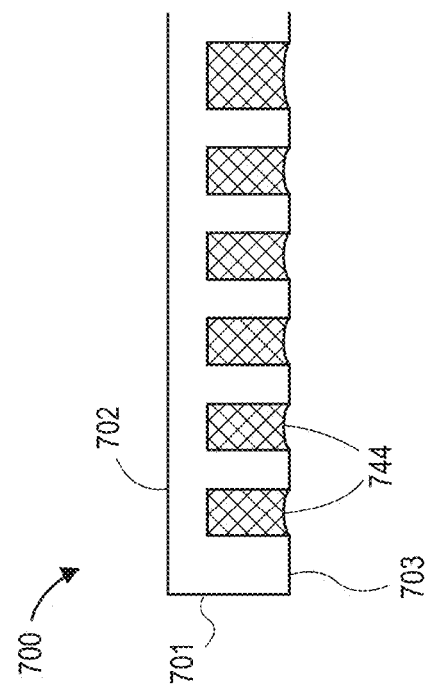
FIG. 7 is a side, elevation view of a semipermeable membrane with backfilled depressions in accordance with an embodiment.

FIG. 7 is a side, elevation view of a semipermeable membrane with backfilled depressions in accordance with an embodiment. In membrane device 700, membrane 701 has thin regions 702 and thick regions 703. Depressions on the bottom side where the thin regions exist are filled with a biocompatible, porous hydrogel 744, which smoothes out the hills and valleys of the back side. This can be used in situations where a smooth surface for cell growth is desired on the back side of the membrane. Cells can grown on both sides of the membrane, as both sides have relatively smooth surfaces compared with the size of the cells to be grown.

Figure 8:
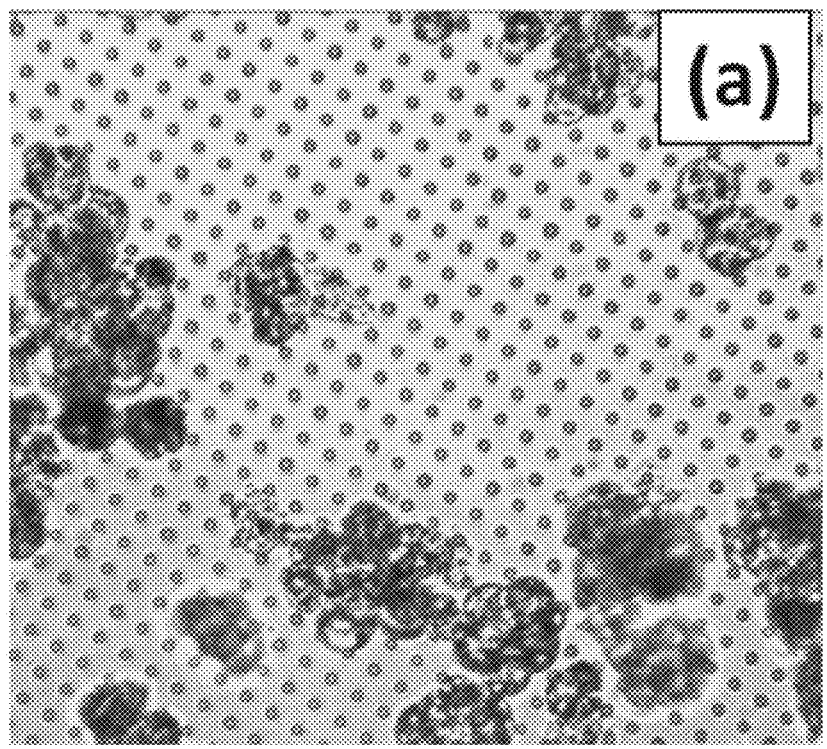
FIG. 8 is an image of cell growth on a porous membrane of the prior art.

FIG. 8 is an image of cell growth on a porous membrane of the prior art, showing H9-RPE (retinal pigment epithelial) cells cultured on a porous parylene-C membrane with oxygen plasma treatment. Note the clumpy adherence of cells, which is undesirable.

Figure 9:
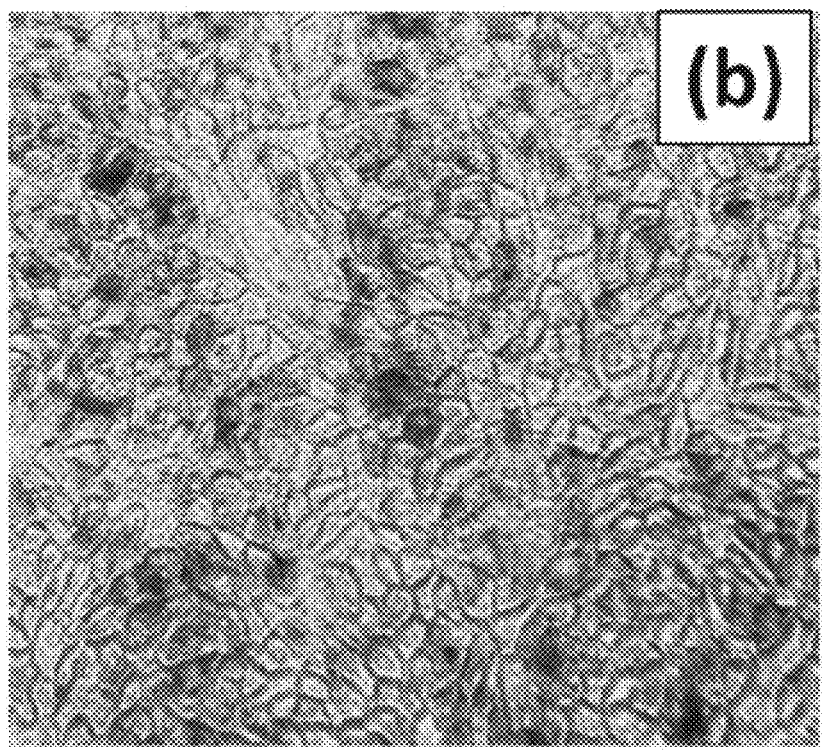
FIG. 9 is an image of cell growth on a semipermeable membrane in accordance with an embodiment.

FIG. 9 is an image of cell growth on a semipermeable membrane in accordance with an embodiment. The cell morphology is very different from that in FIG. 8. In FIG. 9, the cells grow in a relatively flat monolayer, having access to plenty of nutrients through the membrane and able to discharge cell waste through the membrane. The cells proliferated well, became confluent after ten days of culture, and showed clear signs of polarization. The cells also have desirable hexagonal boundaries.

Figure 10:
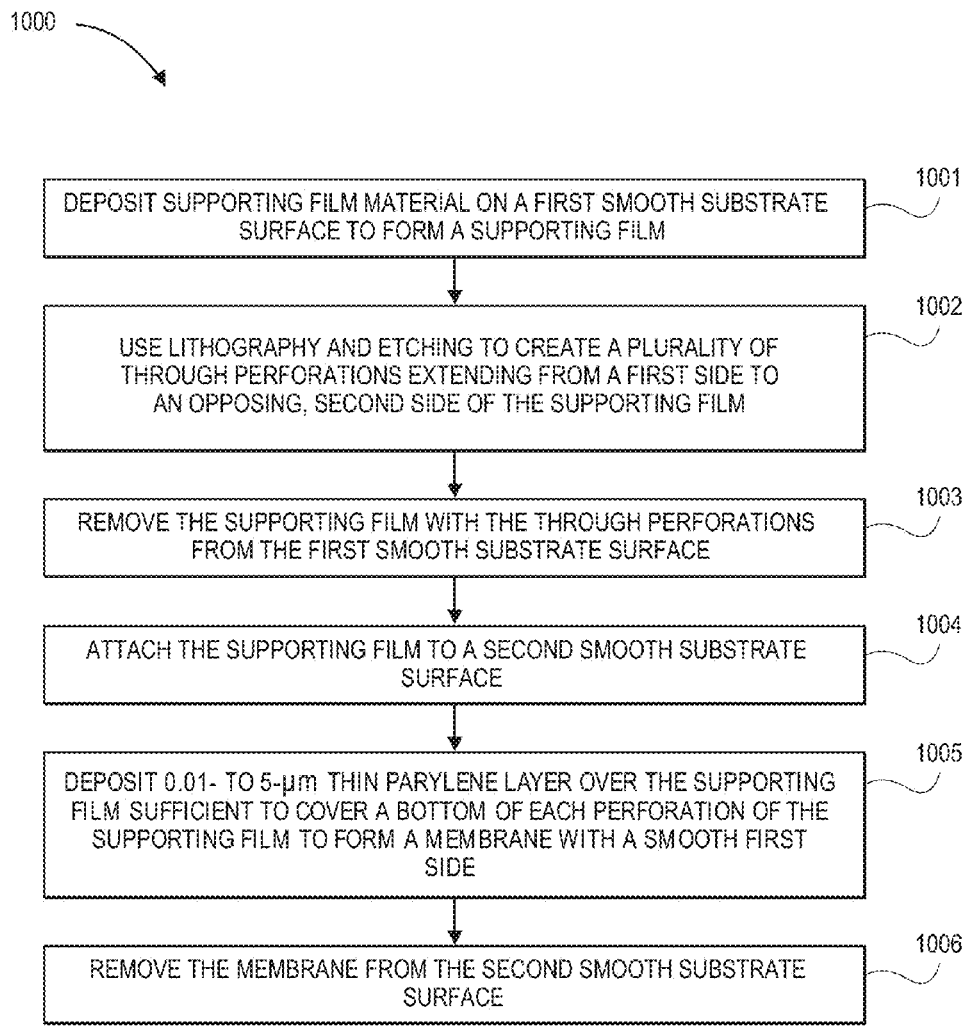
FIG. 10 is a flowchart illustrating a process in accordance with an embodiment.

FIG. 10 is a flowchart illustrating process 1000 in accordance with an embodiment. In operation 1001, a supporting film material is deposited on a first smooth substrate surface to form a supporting film. In operation 1002, lithography and etching are used to create a plurality of through perforations extending from a first side to an opposing, second side of the supporting film. In operation 1003, the supporting film with the through perforations is removed from the first smooth substrate surface. In operation 1004, the supporting film with the through perforations is attached to a second smooth substrate surface. In operation 1005, a 0.01- to 5-μm thin parylene layer is deposited over the supporting film sufficient to cover a bottom of each perforation of the supporting film to form a membrane with a smooth first side. In operation 1006, the membrane is removed from the second smooth substrate surface and readied for implantation.

Figure 11:
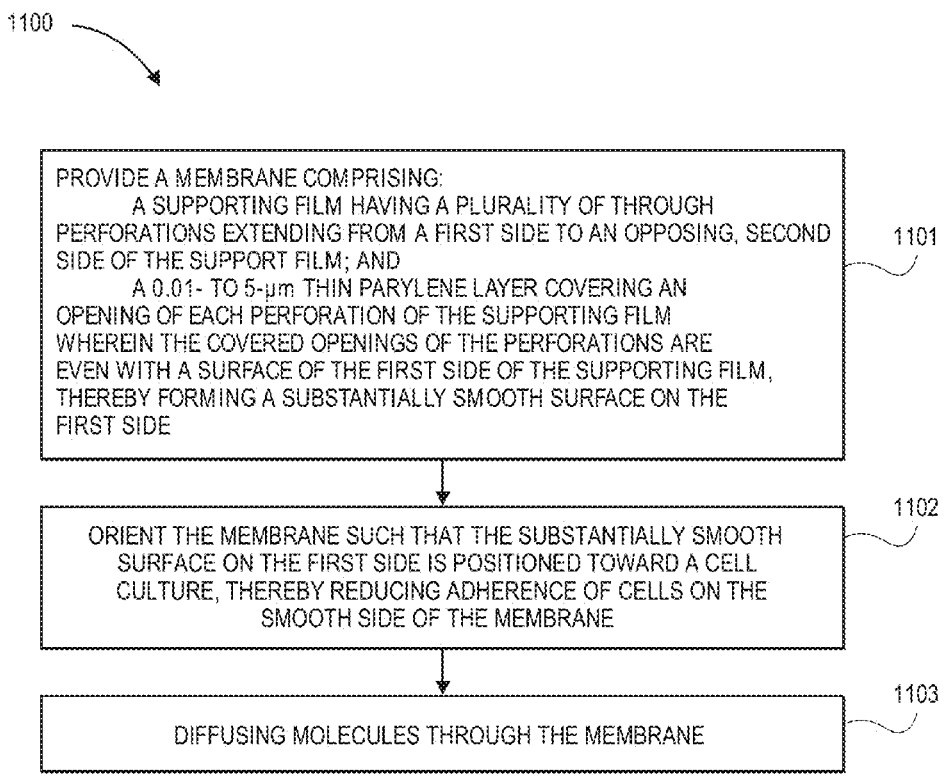
FIG. 11 is a flowchart illustrating a process in accordance with an embodiment.

FIG. 11 is a flowchart illustrating process 1100 in accordance with an embodiment. In operation 1101, a membrane is provided, the membrane comprising: a supporting film having a plurality of through perforations extending from a first side to an opposing second side of the supporting film; and a 0.01- to 5-μm thin parylene layer covering an opening of each perforation of the supporting film wherein the covered openings of the perforations are even with a surface of the first side of the supporting film, thereby forming a substantially smooth surface on the first side. In operation 1102, the membrane is oriented such that the substantially smooth surface on the first side is positioned toward a cell culture, thereby reducing adherence of cells on the smooth side of the membrane. In operation 1103, molecules are diffused through the membrane.

The invention has been described with reference to various specific and illustrative embodiments. However, it should be understood that many variations and modifications may be made while remaining within the spirit and scope of the following claims.

What is claimed is:

1. A synthetic semipermeable membrane apparatus, comprising:
    a membrane having:
        a smooth front side,
        a back side,
        spatially interspersed thin and thick regions between the smooth front side and the back side, and
        a frame substantially surrounding a perimeter of the smooth front side of the membrane,
            the smooth front side facilitating the growth of a monolayer of cells,
            the thicker regions on the back side of the membrane being configured to prevent unwanted cell growth from cells growing on the smooth front side,
            the thin regions being a predetermined thickness of parylene-c,
            the predetermined thickness selected from a thickness between 0.01 μm to 5 μm,
            the thin regions configured to be permeable to protein-sized molecules and impermeable to cells,
            the thick regions comprising parylene-c and being at least 2 times thicker than the predetermined thickness of the thin regions,
            the interspersion of the thin and thick regions occurring in a patterned array with an average feature size of about 1 μm to 30 μm, and
            the frame configured to reduce unwanted migration of cells growing on the smooth front side of the membrane to the back side of the membrane.

2. The apparatus of claim 1 wherein the thin regions of parylene C are between 0.15 μm to 0.8 μm thick, thereby having a molecular weight exclusion limit larger than 70 kDa.

3. The apparatus of claim 1 wherein the interspersion of the thin and thick regions occurring in the patterned array were produced by lithographic etching of the back side of the membrane.

4. The apparatus of claim 1 wherein the predetermined thickness of the thin regions is configured for growing a monolayer of cartilage trabeculae, heart muscle, or retinal pigment epithelium (RPE) cells on the smooth front side.

5. The apparatus of claim 1 wherein the predetermined thickness is selected from a thickness between 0.1 μm to 10 μm.

6. The apparatus of claim 5 wherein the predetermined thickness is about 1 μm and the thick regions are about 3 μm to 6 μm thick,
    thereby allowing diffusion of cell nutrients and cell waste through the membrane to cells.

7. The apparatus of claim 1 wherein the frame being is at least 2 times thicker than the predetermined thickness of the thin regions.

8. The apparatus of claim 1 wherein thick regions near a perimeter of the membrane have relatively sharp features and thick regions toward a center of the membrane have relatively smooth features.

9. The apparatus of claim 1 wherein the thick regions are substantially contiguous with one another and the thin regions comprise recesses in the membrane.

10. The apparatus of claim 9 wherein the thin regions comprise non-through holes in the back side of the membrane.

11. The apparatus of claim 1 wherein the interspersion array is a regular array having a constant feature size.

12. The apparatus of claim 1, wherein the thick regions provide mechanical support to the apparatus.

13. The apparatus of claim 12, wherein the thick regions reduce tearing, folding or undulation of the apparatus during implantation.

14. The apparatus of claim 1, wherein the thin and thick are dimensioned to allow implantation of the apparatus into the eye of a subject to replace a damaged Bruch's membrane.

* * * * *

UNITED STATES PATENT AND TRADEMARK OFFICE
CERTIFICATE OF CORRECTION

PATENT NO. : 8,877,489 B2  
APPLICATION NO. : 13/355426  
DATED : November 4, 2014  
INVENTOR(S) : Yu-Chong Tai Page 1 of 1

It is certified that error appears in the above-identified patent and that said Letters Patent is hereby corrected as shown below:

Title Page

In column 1 (page 2, item 56) at line 28, Under Other Publications, change "Cycloprore" to --Cyclopore--.

In column 1 (page 2, item 56) at line 48, Under Other Publications, change "Microssytems" to --Microsystems--.

In column 1 (page 2, item 56) at line 50, Under Other Publications, change "Reitnal" to --Retinal--.

In column 2 (page 2, item 56) at line 2, Under Other Publications, change "spermatazoa" to --spermatozoa--.

Specification

In column 1 at line 40 (approx.), Change "(gTAS)" to --($\mu$TAS)--.

In column 1 at lines 48-49, Change "polyp-xylylene)" to --poly(p-xylylene)--.

In column 5 at line 45 (approx.), Change "an" to --and--.

In column 8 at line 56, Change "grown" to --grow--.

Signed and Sealed this  
Twenty-seventh Day of October, 2015

Michelle K. Lee  
*Director of the United States Patent and Trademark Office*